United States Patent [19]

Ford

[11] 4,444,775

[45] Apr. 24, 1984

[54] SUBSTITUTED IMIDAZO[1,5-A]PYRIDINES

[75] Inventor: Neville Ford, University City, Mo.

[73] Assignee: Ciba-Geigy Corporation, Ardsley, N.Y.

[21] Appl. No.: 382,972

[22] Filed: Jun. 1, 1982

Related U.S. Application Data

[63] Continuation-in-part of Ser. No. 276,094, Jun. 22, 1981, abandoned.

[51] Int. Cl.$^3$ .................... A61K 31/41; C07D 471/04
[52] U.S. Cl. ...................... 424/256; 546/121
[58] Field of Search ....................... 546/121; 424/256

[56] References Cited

U.S. PATENT DOCUMENTS

| | | | |
|---|---|---|---|
| 4,226,878 | 10/1980 | Tisuka et al. | 424/273 R |
| 4,256,757 | 3/1981 | Hayashi | 424/273 R |
| 4,273,782 | 6/1981 | Cross et al. | 424/273 R |
| 4,361,567 | 11/1982 | Bristol et al. | 424/256 |
| 4,409,226 | 10/1983 | Bristol et al. | 424/256 |

FOREIGN PATENT DOCUMENTS

| | | |
|---|---|---|
| 15171 | 3/1980 | European Pat. Off. . |
| 68386 | 6/1982 | European Pat. Off. . |
| 68386 | 1/1983 | European Pat. Off. . |
| 2016452A | 9/1979 | United Kingdom . |
| 2038821 | 7/1980 | United Kingdom . |

OTHER PUBLICATIONS

Biochemical and Biophysical Research Communications, vol. 112 (3) 899–906 (1983).
O. Fuentes et al., J. Organic Chem. 40, 1210 (1975).
G. D. Durant et al., J. Medicinal Chem. 16, 1272 (1973).
W. W. Paudler et al., J. Heterocyclic Chem. 3, 33 (1966).
P. Blatcher et al., Tetrahedron Letters 21, 2195 (1980).

*Primary Examiner*—Jane T. Fan
*Attorney, Agent, or Firm*—Norbert Gruenfeld

[57] ABSTRACT

Disclosed are e.g. novel 5-(carboxyalkyl)imidazo[1,5-a]pyridines, their derivatives and methods of synthesis. Said compounds are useful as selective thromboxane synthetase inhibitors for the treatment of diseases such as cerebral ischaemia, shock, thrombosis and ischaemic heart disease.

16 Claims, No Drawings

SUBSTITUTED IMIDAZO[1,5-A]PYRIDINES

CROSS REFERENCE TO RELATED APPLICATION

This application is a continuation-in-part of application Ser. No. 276,094 filed June 22, 1981, now abandoned.

BACKGROUND OF THE INVENTION

Imidazo[1,5-a]pyridines reported in the literature are for the most part only functionally substituted on the imidazole portion of the bicyclic ring system. For example 1- and 3-aminoalkyl substituted imidazo[1,5-a]pyridines and tetrahydro derivatives are described in Journal of Medicinal Chemistry 16, 1272–6 (1973). The synthesis of several 5-substituted imidazo [1,5-a]pyridines, e.g. 5-ethoxycarbonyl-imidazo[1,5-a]pyridine, has only been recently described in Tetrahedron letters 21, 2195–6 (1980).

Various substituted imidazoles, e.g. carboxyheptylimidazole (British patent 2,016,452) have been reported as thromboxane synthetase inhibitors.

The present invention is concerned with imidazo [1,5-a]pyridine alkanoic acids and derivatives representing a novel class of suprisingly potent and highly specific thromboxane synthetase inhibitors.

The foregoing advantages and attributes render the imidazo [1,5-a]pyridine derivatives of this invention particularly useful when administered, alone or in combination, to mammals, e.g. for the treatment or prevention of diseases responsive to the inhibition of thromboxane synthetase comprising cardiovascular disorders such as thrombosis, atherosclerosis, cerebral ischaemic attacks, myocardial infarction, angina pectoris, hypertension; respiratory disorders, such as asthma; inflammatory disorders; and migraine headache.

SUMMARY OF THE INVENTION

This invention relates to imidazo[1,5-a]pyridine alkanoic acids, and derivatives useful as selective thromboxane synthetase inhibitors, process for preparing same, pharmaceutical compositions comprising said compounds, and methods of treating diseases responsive to inhibition of thromboxane synthetase by administration of said compounds and compositions to mammals.

Particularly the invention relates to imidazo [1,5-a]pyridines of formula I

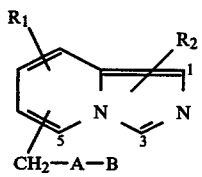

or 5,6,7,8-tetrahydro derivatives thereof, wherein $R_1$ and $R_2$ are hydrogen, halogen, or lower alkyl; A is straight chain or branched alkylene of 1 to 12 carbon atoms, alkynylene or alkenylene of 2 to 12 carbon atoms; B represents carboxy, lower alkoxycarbonyl, unsubstituted or mono- or di-(lower alkyl) substituted carbamoyl, cyano or hydroxymethyl; or salts, especially pharmaceutically acceptable salts thereof.

DESCRIPTION OF THE PREFERRED EMBODIMENTS

Preferred embodiments of this invention relate to compounds of formula I wherein the group $CH_2$—A—B is attached at the 5 position. Very useful as thromboxane synthetase inhibitors are compounds of formula I wherein A is straight or branched alkylene of 1 to 12 carbon atoms.

Particularly useful as thromboxane synthetase inhibitors are compounds of formula II

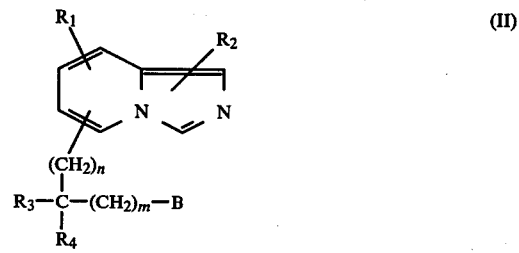

or 5,6,7,8-tetrahydro derivatives thereof, wherein $R_1$, $R_2$, $R_3$ and $R_4$ are hydrogen or lower alkyl of 1 to 4 carbon atoms, n is 1 to 7, m is 0 or 1; B represents carboxy, lower alkoxycarbonyl, unsubstituted or mono- or di-(lower alkyl)substituted carbamoyl, cyano or hydroxymethyl; or pharmaceutically acceptable salts thereof.

Especially useful are compounds of formula II or 5,6,7,8-tetrahydro derivatives thereof, wherein $R_1$, $R_2$, $R_3$, $R_4$ are hydrogen, methyl or ethyl; $(CH_2)_n$ is propylene, butylene, pentylene or hexylene; m is 0 or 1; B represents carboxy, methoxycarbonyl or ethoxycarbonyl, unsubstituted carbamoyl, cyano, monomethyl or monoethylcarbamoyl, dimethyl or diethylcarbamoyl, cyano or hydroxymethyl; or pharmaceutically acceptable salts thereof.

Preferred in turn, are the compounds of formula II wherein the group

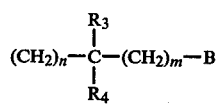

is attached at the 5-position.

Exceedingly useful are compounds of formula III, or 5,6,7,8-tetrahydro derivatives thereof,

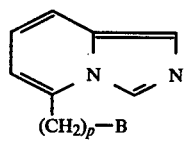

wherein p is 3 to 8; B represents carboxy, lower alkoxycarbonyl, unsubstituted or mono- or di-(lower alkyl) substituted carbamoyl; cyano or hydroxymethyl; or pharmaceutically acceptable salts thereof.

Especially valuable are compounds of formula IV, or 5,6,7, 8-tetrahydro derivatives thereof,

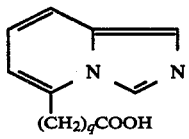

(IV)

wherein q is 4,5 or 6; or pharmaceutically acceptable acid or base addition salts thereof.

The general definitions used herein have the following meanings within the scope of the present invention.

A straight chain or branched alkylene represents $C_{1-12}$ alkylene preferably propylene, butylene, pentylene or hexylene, said radicals being unsubstituted or substituted by one or more lower alkyl groups with the proviso that the total number of carbon atoms equals no more than 12.

The term "straight chain or branched alkenylene" represents $C_{2-12}$ alkenylene preferably propenylene, 1- or 2-butenylene, 1- or 2-pentenylene, 1-, 2- or 3-hexenylene, said radicals being unsubstituted or substituted by one or more lower alkyl groups with the proviso that the total number of carbon atoms equals no more than 12.

The term "straight chain or branched alkynylene" represents $C_2$–$C_{12}$ alkynylene preferably propynylene, 1- or 2-butynylene, 1- or 2-pentynylene, 1-, 2- or 3-hexynylene, said radicals being unsubstituted or substituted by one or more lower alkyl groups with the proviso that the total number of carbon atoms equals no more than 12.

The term "lower" referred to above and hereinafter in connection with organic radicals or compounds respectively defines such with up to and including 7, preferably up and including 4 and advantageously one or two carbon atoms.

A lower alkyl group preferably contains 1–4 carbon atoms and represents for example ethyl, propyl, butyl or advantageously methyl.

A lower alkoxycarbonyl group preferably contains 1–4 carbon atoms in the alkoxy portion and represents for example methoxycarbonyl, propoxycarbonyl, isopropoxycarbonyl or advantageously ethoxycarbonyl. A mono-(lower alkyl)carbamoyl group preferably contains 1–4 carbon atoms in the alkyl portion and is for example N-methylcarbamoyl, N-propylcarbamoyl or advantageously N-ethylcarbamoyl. A di-(lower alkyl)carbamoyl group preferably contains 1–4 carbon atoms in each lower alkyl portion and represents for example N,N-dimethylcarbamoyl, N-methyl-N-ethylcarbamoyl and advantageously N,N-diethylcarbamoyl.

Pharmaceutically acceptable salts are preferably metal or ammonium salts of said compounds of formula I when B represents carboxy, more particularly alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amines, lower alkylenediamines or lower (hydroxyalkyl or aralkyl)-alkylammonium bases, e.g., methylamine, diethylamine, triethylamine, dicyclohexylamine, triethanolamine, ethylenediamine, tris-(hydroxymethyl)-aminomethane or benzyl-trimethylammonium hydroxide. Said compounds of Formula I form acid additon salts, which are preferably such of therapeutically acceptable inorganic or organic acids, such as strong mineral acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, benzenesulfonic, p-toluenesulfonic, naphthalenesulfonic, sulfanilic or cyclohexylsulfamic acid.

The compounds of this invention exhibit valuable pharmacological properties, e.g. cardiovascular effects, by selectively inhibiting the release of thromboxane through selective inhibition of thromboxane synthetase in mammals. The compounds are thus useful for treating diseases responsive to thromboxane synthetase inhibition in mammals including man.

These effects are demonstrable in vitro assay tests or in vivo animal tests using advantageously mammals, e.g. guinea pigs, mice, rats, cats, dogs, or monkeys. Said compounds can be administered to them enterally or parenterally, advantageously orally, or subcutaneously, intravenously or intraperitoneally, for example, within gelatin capsules, or in the form of starchy suspensions or aqueous solutions respectively. The applied dosage may range between about 0.01 and 100 mg/kg/day, preferably between about 0.05 and 50 mg/kg/day, advantageously between about 0.1 and 25 mg/kg/day.

The in vitro inhibition of the thromboxane synthetase enzyme can be demonstrated, analogous to the method of Sun, Biochem. Biophys. Res. Comm. 74, 1432 (1977); the testing procedure is as follows:

$^{14}C$-arachidonic acid is incubated with an enzyme preparation consisting of solubilized and partially purified prostaglandin cyclo-oxygenase from sheep seminal vesicles and a crude microsomal preparation of thromboxane synthetase from lysed human platelets. The test compound (dissolved in buffer, or if necessary, in a small amount of ethanol) is added to the incubation medium. At the end of the incubation period (30 minutes), Prostaglandin $E_2$ ($PGE_2$) is reduced to a mixture of Prostaglandin $F_2\alpha$ and $F_2\beta$ ($PGF_2 \alpha+\beta$) by addition of sodium borohydride. The radioactive products and excess substrate are extracted into ethyl acetate; the extract is evaporated to dryness; the residue is dissolved in acetone, spotted on thin-layer plates and chromatographed in the solvent system toluene: acetone: glacial acetic acid (100 volumes: 100 volumes: 3 volumes). The radioactive zones are located; those corresponding to Thromboxane $B_2$ ($T \times B_2$) and $PGF_2 \alpha+\beta$ are transferred to liquid scintillation vials and counted. The ratio of counts for $T \times B_2/PGF_2 \alpha+\beta$ is calculated for each concentration of test compound and $IC_{50}$ values are determined graphically as the concentration of test compound at which the ratio of $T \times B_2/PGF_2 \alpha+\beta$ is reduced to 50% of the control value.

The in-vitro effect on prostaglandin cyclooxygenase is measured by a modification of the method of Takeguchi et al described in Biochemistry 10, 2372 (1971); the testing procedure is as follows:

Lyophilized sheep seminal vesicle microsomes are utilized as the prostaglandin-synthesizing enzyme preparation. The conversion of $^{14}C$-arachidonic acid to $PGE_2$ is measured. Test compounds (dissolved in buffer, or if necessary, in small amount of ethanol) are added to the incubation mixture. The prostaglandins are extracted and separated by thin-layer chromatography;

the plates are scanned, the radioactive zones corresponding to $PGE_2$ are transferred to liquid scintillation vials and counted for radioactivity. $IC_{50}$ values for inhibition are determined graphically as the concentration of test compound causing a 50% reduction in the amount of $PGE_2$ synthesized.

The in-vitro effect on prostacyclin ($PGI_2$) synthetase is measured analogous to the method of Sun et al., Prostaglandins 14, 1055 (1977);

The testing procedure is as follows:

$^{14}C$-Arachidonic acid is incubated with an enzyme mixture consisting of solubilized and partially purified prostaglandin cyclo-oxygenase from sheep seminal vesicles and crude $PGI_2$ synthetase in the form of a microsomal fraction of bovine aorta.

Test compound (dissolved in buffer, or if necessary, in a small amount of ethanol) is placed in the incubation medium. The reaction mixture is incubated in 100 mM Tris HCl (pH 7.5) for 30 minutes at 37° C., acidified to pH 3 and extracted into ethyl acetate. The extract is evaporated to dryness; the residue is dissolved in acetone, spotted on thin-layer plates and chromatographed in a solvent system described by Sun et al. The radioactive zones are located with a scanner; those corresponding to 6-keto-$PGF_{1}\alpha$ (a stable end product of prostacyclin biotrasformation) and $PGE_2$ are transferred to liquid scintillation vials and counted. The ratio of counts for 6-keto-$PGF_{1}\alpha/PGE_2$ is calculated for each concentration of test compound used. $IC_{50}$ values for inhibition are determined graphically as the concentration of test compound at which the ratio of 6-keto-$PGF_{1}\alpha/PGE_2$ is reduced to 50% of the control value.

The reduction of plasma levels of thromboxane is determined in vivo on administration of the test compound to guinea pigs in the following manner:

Guinea pigs are dosed with vehicle or test drug and injected intraperitoneally with arachidonic acid (40 mg/kg) 2 hours later. Blood is collected for analysis 1 hour after the arachidonic acid challenge. A single aliquot of each plasma sample is assayed for thromboxane $B_2$ and another aliquot for 6-keto-$PGF_{1}\alpha$, the stable metabolites of thromboxane $A_2$ and prostacyclin ($PGI_2$) respectively.

The compounds of the formula I are very potent thromboxane synthetase inhibitors. At effective dose levels and greater, the beneficial prostacyclin synthetase enzyme system is not inhibited, nor is the prostaglandin cyclooxygenese enzyme system.

The $IC_{50}$ for a compound of the invention, e.g. 5-(5-carboxypentyl)-imidazo[1,5-a]pyridine of example 2, is about $3\times10^{-9}$ M for thromboxane synthetase inhibition whereas the $IC_{50}$ for both inhibition of prostacyclin synthetase and cyclooxygenase is greater than $1\times10^{-4}$ M.

A compound of the invention, e.g. 5-(5-carboxypentyl)imidazo[1,5-a]pyridine of example 2, also reduces the plasma levels of thromboxane $B_2$ by over 50% in the guinea pig at an oral dose as low as 0.25 mg/kg; no significant decrease with respect to prostacyclin is observed at the said oral dose or at higher doses.

The aforementioned advantageous properties render the compounds of this invention of great value as specific therapeutic agents for mammals including man.

For example, in thromboembolism, specific inhibition of the enzyme thromboxane synthetase reduces arachidonic acid induced platelet aggregation involved in clot formation. Experimentally, prolongation of bleeding time in the rat is indicative of a beneficial antithrombotic effect. The imidazo[1,5-a]pyridines of this invention prolong bleeding time, e.g. 5-(5-carboxypentyl)-imidazo[1,5-a]pyridine prolongs bleeding time when administered to rats at a dose of about 1 mg/kg i.p. or lower.

Indicative of the beneficial effect in respiratory disorders, the compounds of this invention afford protection against sudden death due to arachidonic acid induced pulmonary obstruction, e.g. 5-(5-carboxypentyl)-imidazo[1,5-a]pyridine protects against sudden death when administered orally to mice at a dose of 100 mg/kg.

The compounds of formula I are prepared advantageously according to process 1.

Process 1

(a) condensing a compound of the formula VI

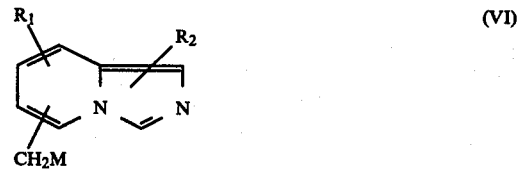

wherein M is an alkali metal; $R_1$ and $R_2$ represent hydrogen or lower alkyl, with a reactive functional derivative of a compound of the formula VII

wherein A is straight chain or branched alkylene of 1 to 12 carbon atoms, alkynylene or alkenylene of 2 to 12 carbon atoms; B' represents carboxy, trialkoxymethyl, unsubstituted or mono- or di-(lower alkyl) substituted carbamoyl, cyano, etherified hydroxymethyl or halomethyl; to yield a compound of formula Ia

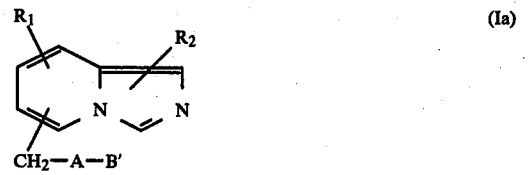

wherein A, B', $R_1$ and $R_2$ have meaning given above;

(b) converting any resulting product wherein B' differs from B, into a compound of formula I; and, if desired (c) converting any resulting compound of formula I into another compound of this invention.

Reactive organometallic compounds of formula VI wherein M is an alkali metal are obtained by metallization of the appropriate methyl substituted imidazo[1,5-a]pyridine, e.g. 5-methylimidazo[1,5-a]pyridine, prepared as described in the Journal of Organic Chemistry 40, 1210 (1975), with a reactive metallizing agent, e.g. butyl lithium or lithium diisopropylamide in an inert solvent such as tetrahydrofuran at a temperature below room temperature preferably at about −50°.

Condensation of the intermediate of formula VI with reactive functional derivatives of a compound of formula VII proceeds at a temperature range preferably from about −75° to +50°. In the case where B' represents carboxy or mono(lower-alkyl)carbamoyl, the appropriate metal salt, e.g. the lithium salt, of the reactive functional derivative of the corresponding compound of formula VII is first prepared for the condensation with intermediate VI.

Alternately compounds of formula I can also be prepared by processes 2, 3 or 4.

Process 2

(a) Condensing a compound of formula VIII

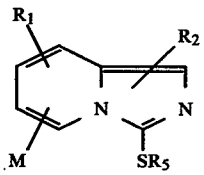
(VIII)

wherein M is an alkali metal, $R_1$ and $R_2$ represent hydrogen or lower alkyl, $R_5$ is lower alkyl
with a reactive functional derivative of a compound of the formula IX

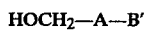
$HOCH_2-A-B'$ (IX)

wherein A is straight chain or branched alkylene of 1 to 12 carbon atoms alkynylene or alkenylene of 2 to 12 carbon atoms; B' represents carboxy, trialkoxymethyl, unsubstituted or mono- or di-(lower alkyl) substituted carbamoyl, cyano, etherified hydroxymethyl or halomethyl;

(b) converting any resulting product wherein B' differs from B into a compound with a group B;
(c) desulfurizing the resulting compound; and, if desired,
(d) converting any resulting compound into another compound of this invention.

Preparation of the organometallic intermediate VIII and subsequent condensations are carried out as described under process 1 supra and in Tetrahedron Letters 21, 2195–6 (1980). Desulfurization is preferably performed with a desulfurization catalyst such as Raney nickel in a solvent such as ethanol, preferably at elevated temperature.

Process 3

(a) condensing under basic catalysis a compound of the formula X

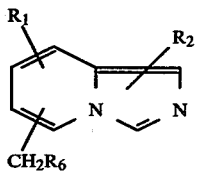
(X)

wherein $R_1$ and $R_2$ represents hydrogen or lower alkyl; and $R_6$ represents lower alkoxycarbonyl or cyano;
with a reactive functional derivative of a compound of the formula VII

$HO-A-B'$ (VII)

wherein A is straight chain or branched alkylene of 1 to 12 carbon atoms, alkynylene or alkenylene of 2 to 12 carbon atoms; B' represents carboxy, trialkoxymethyl, unsubstituted or mono- or di-(lower alkyl) substituted carbamoyl, cyano, etherified hydroxymethyl or halomethyl;

(b) hydrolyzing, decarboxylating the resulting product;
(c) converting any resulting compound wherein B' differs from B into a compound of formula I; and, if desired,
(d) converting any resulting compound of formula I into another compound of the invention.

The intermediates of formula X are prepared from the compound of formula VI supra on treatment with e.g. carbon dioxide and esterfying the resulting carboxylic acid, or with a di-(lower)alkyl carbonate or with a cyanogen halide.

Process 4

(a) cyclizing a compound of formula XI

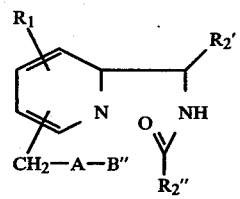
(XI)

wherein R, $R_2'$, and $R_2''$ represent hydrogen or lower alkyl; A has meaning given above; and B'' represents carboxy, lower alkoxycarbonyl, unsubstituted or mono- or di-(lower alkyl) substituted carbamoyl, cyano, hydroxymethyl, lower alkanoyloxymethyl, etherified hydroxymethyl or halomethyl; to yield a compound of formula Ib

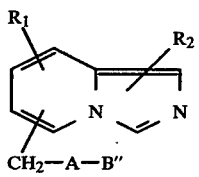
(Ib)

(b) converting any resulting compound wherein B'' differs from B into a compound of formula I; and if desired
(c) converting any resulting compound of formula I into another compound of the invention.

The cyclization of the amide of formula XI is advantageously carried out under conditions such as described for the cyclization of 6-methyl-2-methylaminopyridine to 5-methylimidazo[1,5-a]pyridine in J. Org. Chemistry 40, 1210 (1975). Said cyclization may be achieved advantageously with a Lewis acid, such as polyphosphoric acid, phosphorous oxychloride, polyphosphate ester, optionally in an inert solvent such as toluene, at a temperature range of 25° to 150°, preferably 50° to 120° C.

The amides of formula XI are prepared by acylating a compound of formula XII

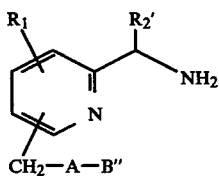

(XII)

wherein R, $R_2'$, A and B" have meaning given above, with a carboxylic acid of the formula XIII, $R_2''COOH$ (XIII)

wherein $R_2''$ has meaning given above, or with a reactive functional derivative thereof.

Reactive functional derivatives of compounds XIII are preferably acid halides, simple or mixed anhydrides, such as the acid chloride, the acid anhydride $(R_2''CO)_2O$, or a mixed anhydride derived from a lower alkoxycarbonyl halide, such as ethyl chloroformate, or from a hindered lower alkanoyl halide, e.g., from pivaloyl chloride, by methods well-known to the art.

Said condensation of compounds XII and XIII (the acylation of XII) occurs either spontaneously by e.g. heating with formic acid, or in the presence of condensing agents, e.g. disubstituted carbodiimides, such as dicyclohexylcarbodiimide.

The acylation of compounds of formula XII with a reactive functional derivative of XIII, e.g. acetyl chloride or acetic anhydride, occurs advantageously in the presence of an organic or inorganic base, e.g., potassium carbonate, triethylamine.

The amines of formula XII may be obtained, e.g. from the correspondingly substituted 2-(cyano, or lower hydroxyiminoalkyl) pyridines by reduction, e.g. by hydrogenation in the presence of a catalyst such as palladium on charcoal or by treatment with a chemical reducing agent such as borane or sodium cyanoborohydride, the reducing agent being chosen according to the type of other functional groups present in the molecule. The compounds of formula XII may also be obtained by amination of the correspondingly substituted and reactively esterified 2-(hydroxymethyl)pyridines.

Certain terms used in the foregoing processes have the meanings as defined below.

Reactive functional derivative of alcohols of formula VII and IX are e.g. such esterified by a strong inorganic or organic sulfonic acid above all a hydrohalic acid, e.g. hydrochloric, hydrobromic or hydriodic acid, an aliphatic or aromatic sulfonic acid, e.g. methanesulfonic acid, p-toluenesulfonic acid, and are prepared by methods known in the art.

Trialkoxymethyl represents preferably tri(lower alkoxy)methyl, particularly triethoxy- or trimethoxymethyl.

Etherified hydroxymethyl represents preferably tertiary lower alkoxymethyl, lower alkoxyalkoxymethyl such as methoxymethoxymethyl, 2-oxa- or 2-thiacycloalkoxymethyl particularly 2-tetrahydropyranyloxymethyl.

Halomethyl represents especially chloromethyl but may also be bromomethyl or iodomethyl.

Lower alkanoyloxymethyl represents preferably acetoxymethyl.

An alkali metal represents preferably lithium but may also be potassium or sodium.

The conversion of any inital product [part a] of the aforesaid processes wherein B' or B" differs from B into a compound of formula I, and the optional conversion of the resulting product of formula I into another compound of this invention are performed by chemical methodology known to the art.

Hydrolysis of intermediates wherein B' represents trialkoxymethyl to compounds of formula I wherein B is carboxy is advantageously carried out with inorganic acids such as hydrohalic or sulfuric acid. Hydrolysis of intermediates wherein B' represents etherified hydroxymethyl to compounds of formula I wherein B represents hydroxymethyl is preferably carried out with solutions of inorganic acids such as a hydrohalic acid.

Intermediates of formula Ia or Ib wherein B' or B" is halomethyl may be reacted preferably with a metal cyanide such as potassium cyanide in a conventional manner to yield the compounds of formula I wherein the chain is extended by 1 carbon atom and B is cyano. These in turn are converted to compounds of formula I wherein B is carboxy, alkoxycarbonyl or carbamoyl using methods known to the art.

Thus, the compounds of formula I wherein B represents cyano (nitriles) are converted to compounds of formula I wherein B is carboxy by hydrolysis with inorganic acids e.g. a hydrohalic acid such as hydrochloric acid or sulfuric acid in aqueous solution, or advantageously by hydrolysis with aqueous alkali metal hydroxide e.g. potassium hydroxide at reflux temperature.

The conversion of said nitriles to compounds of formula I wherein B represents lower alkoxycarbonyl is advantageously carried out by treatment first with a lower alkanol, e.g. anhydrous ethanol, in the presence of a strong acid, e.g. hydrochloric acid preferably at reflux temperature, followed by careful hydrolysis with water.

Furthermore the conversion of the said nitriles to compounds of formula I wherein B represents carbamoyl is preferably carried out by treatment with an alkali metal hydroxide, e.g. dilute sodium hydroxide, and hydrogen peroxide, preferably at room temperature.

Furthermore, the intermediates of formula Ia or Ib wherein B' or B" is halomethyl, such as chloromethyl, are converted to compounds of formula I, wherein B is carboxy and the chain length is extended by two carbons, by first treating with e.g. a di-(lower)alkyl malonate, such as diethyl malonate, in the presence of a base such as potassium carbonate or sodium ethoxide, in a solvent such as dimethylformamide, preferably at a temperature range from 50° to 100°. The resulting substituted di(lower)alkyl malonate is hydrolyzed, advantageously with aqueous base, such as dilute sodium hydroxide, to the corresponding malonic acid which is decarboxylated under standard conditions, e.g. by heating in xylene solution, to give a compound of formula I wherein B is carboxy. Substitution of the di-(lower)alkyl malonate with a lower alkyl cyanoacetate yields the corresponding compounds of formula I wherein B is cyano.

Compounds of the invention, wherein A represents straight chain or branched alkenylene with a terminal double bond, may also be prepared from intermediates of formula Ia or Ib wherein B' or B" is halomethyl. For instance, said intermediates are first treated with e.g. a lower alkyl ester of an α-(aryl- or alkyl)-thioacetic acid such as ethyl α-(phenylthio)-acetate, in the presence of a strong base such as sodium hydride. Subsequent oxidation of the resulting α-arylthio or α-alkylthio substituted ester to the α-arylsulfinyl or α-alkylsulfinyl ester with e.g. sodium periodate, followed by heat-induced elimination, by e.g. refluxing in xylene, yields a compound of general formula I (an αβ-unsaturated ester) wherein A represents alkenylene and B represents e.g. lower alkoxycarbonyl, and the chain length has been extended by two carbon atoms. Similarly, the compounds of formula Ia wherein B represents halomethyl may first be converted to the corresponding carboxaldehydes with e.g. dimethylsulfoxide in the presence of triethylamine and silver tetrafluoroborate. Subsequent Wittig condensation e.g. with ethyl (triphenylphosphorarylidene)-acetate also yields the above-cited αβ-unsaturated esters.

Compounds of formula I wherein B is lower alkoxycarbonyl may be amidized with ammonia, mono- or di-(lower) alkylamines e.g. methylamine, dimethylamine in an inert solvent, e.g. a lower alkanol, such as butaniol, optionally at elevated temperatures to yield compounds of formula I wherein B represents unsubstituted, mono- or di-(lower) alkylcarbamoyl.

The compounds of formula I wherein B represents unsubstituted carbamoyl may be dehydrated to the corresponding nitrile by treatment with e.g. triphenylphosphine or thionyl chloride in an inert solvent such as toluene.

Conversion of compounds of formula I wherein B is lower alkoxycarbonyl; cyano; unsubstituted, mono- or di-(lower alkyl)carbamoyl to compounds of formula I wherein B represents carboxy is advantageously carried out by hydrolysis with inorganic acids such as hydrohalic or sulfuric acid or with aqueous alkalies, preferably alkali metal hydroxides such as lithium or sodium hydroxide.

Compounds of formula I wherein B represents carboxy or lower alkoxycarbonyl may be reduced with simple or complex light metal hydrides such as lithium aluminum hydride, alane or diborane to compounds of formula I wherein B is hydroxymethyl. Said alcohols are also obtained by appropriate solvolysis of compounds of formula Ia or Ib wherein B' or B'' is halomethyl by treatment with e.g. an alkali metal hydroxide such as lithium or sodium hydroxide.

Said alcohols may in turn be transformed to the compounds of formula I wherein B is carboxy with conventional oxidizing agents, advantageously with pyridinum dichromate in dimethylformamide at room temperature.

Free carboxylic acids may be esterified with lower alkanols such as ethanol in the presence of a strong and e.g. sulfuric acid advantageously at elevated temperature or with diazo (lower) alkanes, e.g. diazomethane in a solvent such as ethyl ether, advantageously at room temperature, to give the corresponding esters, namely compounds of formula I wherein B is lower alkoxycarbonyl.

Furthermore, the free carboxylic acids may be converted via treatment of a reactive intermediate thereof, e.g. an acyl halide such as the acid chloride, or a mixed anhydride, e.g. such derived from a lower alkyl halocarbonate such as ethyl chloroformate, with ammonia, mono- or di-(lower) alkylamines, in an inert solvent such as methylene chloride, preferably in the presence of a basic catalyst such as pyridine, to compounds of formula I wherein B represents unsubstituted, mono or di-(lower)alkylcarbamoyl.

Compounds of formula I wherein B represents mono(lower) alkylcarbamoyl are converted to compounds of formula I wherein B is di-(lower)alkyl-carbamoyl by treatment of the former with a strong base e.g. sodium hydride followed by an alkylating agent, e.g. a lower alkyl halide in an inert solvent, e.g. dimethylformamide.

Compounds of formula I are converted to the corresponding 5, 6, 7, 8-tetrahydroimidazo[1,5-a]pyridine compounds by reduction with hydrogen in the presence of a hydrogenation catalyst, e.g. palladium, and an acid e.g. a mineral acid, for instance hydrochloric acid in an inert solvent, e.g. ethanol.

Furthermore compounds of formula I wherein A represents a straight chain or branched alkynylene or alkenylene may be converted by catalytic hydrogenation, advantageously under neutral conditions e.g. with palladium catalyst at atmospheric pressure in an inert solvent, e.g. ethanol, to compounds of formula I wherein A represents straight chain or branched alkylene.

Furthermore compounds of formula I wherein $R_1$ and $R_2$ represent hydrogen can be converted to the corresponding halo derivatives by direct halogenation with chlorine, bromine or iodine.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditons, or in which the reaction components are used in the form of their salts or optically pure antipodes. Mainly those starting materials should be used in said reactions, that lead to the formation of those compounds indicated above as being especially useful.

The invention also relates to novel starting materials and processes for their manufacture.

Depending on the choice of starting materials and methods, the new compounds may be in the form of one of the possible isomers or mixtures thereof, for example, depending on the presence of a double bond and the number of asymmetrical carbon atoms, as pure optical isomers, such as antipodes, or as mixtures of isomers, such as racemates, mixtures of diastereoisomers, mixtures of racemates or mixtures of geometrical isomers.

Resulting mixtures of diastereoisomers, mixtures of racemates and geometric isomers can be separated on the basis of the physicochemical differences of the constituents, in known manner, into the pure isomers, diastereoisomers, racemates, or geometric isomers for example by chromatography and/or fractional crystallisation.

Resulting racemates can furthermore be resolved into the optical antipodes by known methods, for example by recrystallisation from an optically active solvent, by means of microorganisms or by reacting an acidic end product with an optically active base that forms salts with the racemic acid, and separating the salts obtained in this manner, for example on the basis of their different solubilities, into the diastereoisomers, from which the antipodes can be liberated by the action of suitable agents. Basic racemic products can likewise be resolved into the antipodes, for example, by separation of diastereomeric salts thereof, e.g. by the fractional crystallization of d- or l-tartrates.

Advantageously, the more active of the two antipodes is isolated.

Finally, the compounds of the invention are either obtained in the free form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide or a basic salt, e.g. an alkali metal hydroxide or carbonate, or a cation exchange preparation. A compound of formula I wherein B represents carboxy can thus also be converted into the corresponding metal or ammonium salts. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for the crystallisation.

The pharmaceutical compositions according to the invention are those suitable for enteral, such as oral or rectal, and parenteral administration to mammals, including man, for the treatment or prevention of diseases responsive to inhibition of thromboxane synthetase such as peripheral vascular diseases, comprising an effective amount of a pharmacologically active compound of formula I, or pharmaceutically acceptable salts thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweetners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A unit dosage for a mammal of about 50 to 70 kg may contain between about 10 to 200 mg of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mmHg.

EXAMPLE 1

To a solution of 50 g of 5-methylimidazo[1,5-a]pyridine [J. Org. Chem. 40, 1210 (1975)] in 625 ml of tetrahydrofuran precooled to −75° is added under nitrogen atmosphere 175 ml of 2.4 N n-butyllithium in hexane while maintaining temperature below −53°. The solution of 5-(lithiomethyl)imidazo[1,5-a]pyridine, is cooled back to −75° and a solution of 121.8 g of 5-bromo-1,1,1-triethoxypentane in 125 ml of tetrahydrofuran is added rapidly at which time the temperature rises to −60°. The reaction mixture is allowed to warm to −4° over a 45 minute period and evaporated practically to dryness. The residue is partitioned between 500 ml of ethyl ether and 240 ml of 3 N hydrochloric acid. The ether solution is further extracted twice with 60 ml of 3 N hydrochloric acid; the combined aqueous extract is basified with 100 ml of concentrated ammonia hydroxide and reextracted twice with 200 ml of ethyl ether. The ether extract is dried over magnesium sulfate and evaporated to dryness to give an oil which is distilled under high vacuum to give 5-(5-ethoxycarbonylpentyl)-imidazo[1,5-a]pyridine boiling at 180°-5°/0.12 mm Hg.

EXAMPLE 2

A suspension of 26 g of 5-(5-ethoxycarbonylpentyl)imidazo[1,5-a]pyridine in 100 ml of 1 N aqueous sodium hydroxide solution is heated on a steam bath for two hours; 10 ml of ethanol is added and heating is continued for 45 minutes. The reaction mixture is cooled, washed with 300 ml of ether and the solution is adjusted to pH 5.5 with concentrated hydrochloric acid. The crystallized product is collected by filtration and washed with 50 ml of water to yield 5-(5-carboxypentyl)-imidazo[1,5-a]pyridine melting at 144°-7°.

EXAMPLE 3

(a) To a solution of 39.6 g of 5-bromovaleric acid in 400 ml of tetrahydrofuran cooled to −78° is added slowly 93 ml of 2.3 N n-butyl lithium solution in hexane so as to maintain the temperature below −65°. The suspension is stirred for 20 minutes. Then a solution of 5-(lithiomethyl)imidazo[1,5-a]pyridine, prepared from 26.9 g of 5-methylimidazo[1,5-a]pyridine and 93 ml of 2.3 N n-butyl lithium solution as described in example 1, is added all at once at −75°. The reaction mixture is stirred at −75° for two hours, allowed to warm to room temperature, treated with 15 ml of 12 N hydrochloric acid, and evaporated under vacuum.

The residue is partitioned between water and methylene chloride after pH is adjusted to 10. The aqueous solution is further washed with chloroform, acidified to pH 1 and again washed with ether and toluene. After pH is adjusted to 5.5, extraction with chloroform gives crude 5-(5-carboxypentyl)imidazo-[1,5-a]pyridine. A solution of the acid in 30 ml of acetonitrile is treated with 5 N ethanolic hydrochloric acid. After addition of 25 ml of ethyl ether, 5-(5-carboxypentyl)imidazo[1,5- a]pyridine hydrochloride, melting at 201°–4°, crystallizes. 5-(5-Carboxypentyl)-imidazo[1,5-a]pyridine (example 2) is obtained on neutralization of a methanolic solution of the salt to pH 5.

(b) Similarly prepared from 6-bromohexanoic acid is 5-(6-carboxyhexyl)-imidazo[1,5-a]pyridine melting at 137°–9°.

(c) 5-(7-carboxyheptyl)-imidazo[1,5-a]pyridine melting at 97°–101° is similarly prepared from 7-bromoheptanoic acid.

EXAMPLE 4

A solution of 37 g of 5-(5-chloropentyl)-imidazo[1,5-a]pyridine, 21.7 g of potassium cyanide and 3 g of dibenzo-18-crown-6 in acetonitrile is heated under reflux for 20 hours. The acetonitrile is evaporated under reduced pressure, the residue is partitioned between water and methylene chloride, and the methylene chloride extract is evaporated to dryness. Treatment of a solution of the residue in ether with ethanolic hydrochloric acid yields 5-(5-cyanopentyl)-imidazo[1,5-a]pyridine hydrochloride melting at 178°–80°.

The starting material is prepared as follows:

A solution of 30 g of 1-bromo-4-chlorobutane in 20 ml of dry tetrahydrofuran is added to a solution of 5-(lithiomethyl)imidazo[1,5-a]pyridine (prepared from 22 g of 5-methylimidazo[1,5-a]pyridine and 80 ml of 2.3 N solution of n-butyl lithium in hexane according to example 1) while maintaining the temperature below −50°. The reaction mixture is stirred for 2 to 3 hours at −50°, allowed to warm to room temperature, stirred overnight, and evaporated to dryness.

The solution of the residue in methylene chloride is washed with water, dried over magnesium sulfate and evaporated to dryness to give the 5-(5-chloropentyl)-imidazo[1,5-a]pyridine which is used without further purification.

EXAMPLE 5

5-(4-chlorobutyl)-imidazo[1,5-a]pyridine is converted in a manner analogous to that described for Example 4, to 5-(4-cyanobutyl)-imidazo[1,5-a]pyridine melting at 72°–77°.

EXAMPLE 6

By a procedure analogous to that described for example 4, 3,5-dimethylimidazo[1,5-a]pyridine [J. Het. Chem. 3,33 (1966)]is converted to 5-(5-chloropentyl)-3-methyl-imidazo[1,5-a]pyridine, melting at 98°–104°. Reaction with potassium cyanide, under the conditions of example 4, and treatment with ethanolic hydrogen bromide yields the 5-(5-cyanopentyl)-3-methylimidazo[1,5-a]pyridine hydrobromide melting at 215°–220°.

EXAMPLE 7

A solution of 36 g of 5-(cyanopentyl)-imidazo[1,5-a]pyridine in 100 ml of methanol and 50 ml of 45% aqueous potassium hydroxide solution is heated under reflux for 48 hours. The methanol is removed by evaporation under reduced pressure, and water is added. The basic solution is washed with ethyl acetate and acidified to pH 5.5–6 with concentrated hydrochloric acid.

The crystallized acid is collected, and recrystallized from ethanol to yield the product of example 2, namely the 5-(5-carboxypentyl)-imidazo[1,5-a]pyridine melting at 142°–5°, further recrystallization raises the melting point to 144°–7°.

EXAMPLE 8

Hydrolysis of 5-(4-cyanobutyl)-imidazo[1,5-a]pyridine as described for example 7 yields 5-(4-carboxybutyl)-imidazo[1,5-a]pyridine melting at 161°–3°.

EXAMPLE 9

Hydrolysis as described for example 7, of 5-(5-cyanopentyl)-3-methyl-imidazo[1,5-a]pyridine yields 5-(5-carboxypentyl)-3-methyl-imidazo[1,5-a]pyridine melting at 170°–3°.

EXAMPLE 10

To a solution of 3 g of 5-(5-cyanopentyl)-3-methyl-imidazo[1,5-a]pyridine hydrochloride in a mixture of 20 ml of ethanol and 5 ml of 1 N sodium hydroxide solution is added 10 ml of 30% hydrogen peroxide solution; 5 ml of ethanol and a sufficient volume of 1 N sodium hydroxide solution to reach pH 10 are then added.

After stirring at room temperature overnight, the ethanol is evaporated under reduced pressure, water is added and the mixture is extracted with methylene chloride. The resulting product is crystallized from ether and recrystallized from acetonitrile to yield 5-(5-carbamoylpentyl)-imidazo[1,5-a]pyridine melting at 131°–2°.

EXAMPLE 11

A solution of 3.9 g of 5-(5-ethoxycarbonylpentyl)-imidazo[1,5-a]pyridine in 40 ml of n-butanol is saturated with methylamine and heated on a steam bath for 56 hours in a pressure bottle. The reaction mixture is evaporated to dryness; the resulting product is first crystallized from ether and then recrystallized from 1:1 ethyl acetate-ether to yield the 5-[5-(N-methylcarbamoyl)-pentyl]-imidazo[1,5-a]pyridine melting at 118°–22°.

EXAMPLE 12

A solution of 2.45 g of 5-[5-(N-methylcarbamoyl)pentyl]imidazo[1,5-a]pyridine in 25 ml of dimethylformamide is treated with 0.011 mole of sodium hydride (obtained by washing 0.53 g of 50% NaH dispersion in mineral oil with hexane) and warmed briefly on a steam bath. Methyl iodide (1.56 g) is added to the cooled yellow solution. The mixture is stirred at room temperature for 2 hours, diluted with water and extracted first with a 1:1 mixture of ethyl acetate and ether and subsequently with chloroform. The residue obtained on evaporation of the combined extracts to dryness is dissolved in ether and treated with ethanolic hydrochloric acid. The precipitated salt is collected, recrystallized first from acetonitrile/ethyl acetate and then from ethanol/ether to yield 5-[5-(N,N-dimethylcarbamoyl)-pentyl]imidazo[1,5-a]pyridine hydrochloride melting at 166°–71°.

EXAMPLE 13

5-(5-Carboxypentyl)-imidazo[1,5-a]pyridine (1.0 g) is suspended in 5 ml of tetrahydrofuran. While stirring at room temperature, 2.35 g of trimethyl borate is added, followed by the slow addition of 1.0 ml (equivalent to 0.01 mole) of boranemethyl sulfide complex. The reaction mixture is heated at reflux temperature for 2 hours, cooled and quenched by the addition of 2.6 ml of methanol, 9.5 ml of water and 2 ml of 50% sodium hydroxide.

After heating under reflux for 1 hour, the mixture is diluted with water, extracted twice with methylene chloride. The methylene chloride extract is evaporated to dryness. The residue is treated with ethanolic hydrochloric acid in ether to yield the 5-(6-hydroxyhexyl)-imidazo[1,5-a]pyridine hydrochloride melting at 174°–9°.

EXAMPLE 14

A solution of 11.1 g of 1-tetrahydropyranyloxy-8-bromooctane in 15 ml of tetrahydrofuran is added at −70° to a solution of 5-(lithiomethyl)-imidazo[1,5-a]pyridine (prepared from 5 g of 5-methylimidazo[1,5-a]pyridine and 17.7 ml of 2.3 N n-butyl lithium in hexane according to example 1). The mixture was stirred at −70° for 1 hour and then stirred overnight without additional cooling. A solution of the residue (after evaporation to dryness) in 4 N hydrochloric acid is washed with ether, basified with aqueous sodium hydroxide solution and extracted twice with methylene chloride. The methylene chloride extract is evaporated to dryness. Conversion to the hydrochloride salt with ethereal hydrogen chloride and recrystallization from ethanol/ether yields 5-(9-hydroxynonyl)-imidazo[1,5-a]pyridine hydrochloride melting at 150°–3°.

EXAMPLE 15

(a) A solution of 2.7 g of 5-(6-carboxyhexyl)-imidazo[1,5-a]pyridine in a mixture of 120 ml of ethanol and 30 ml of concentrated hydrochloric acid is hydrogenated at 3 atmospheres in the presence of 1 g of 10% palladium on charcoal catalyst until 2 moles of hydrogen are consumed. The mixture is filtered free of catalyst and evaporated to dryness. The residue is recrystallized from isopropanol-ether to yield the 5-(6-carboxyhexyl)-5,6,7,8-tetrahydroimidazo[1,5-a]pyridine hydrochloride melting at 150°–4°.

(b) Similar hydrogenation of 5-(5-carboxypentyl)-imidazo[1,5-a]pyridine yields 5-(5-carboxypentyl)-5,6,7,8-tetrahydroimidazo[1,5-a]pyridine hydrochloride melting at 146°–50°.

(c) Similar hydrogenation of 5-(4-carboxybutyl)-imidazo[1,5-a]pyridine yields 5-(4-carboxybutyl)-5,6,7,8-tetrahydroimidazo[1,5-a]pyridine hydrochloride melting at 120°–3°.

EXAMPLE 16

A solution of 2.3 g (0.011 mole) of 5-bromo-3,3-dimethylpentanoic acid [J. Org. Chem. 44, 1258 (1979)] in 20 ml of dry tetrahydrofuran is cooled to −70° under nitrogen, 5.05 ml of 2.4 M n-butyllithium in hexane is added dropwise. After addition is complete the solution of 5-(lithiomethyl)-imidazo[1,5-a]pyridine in hexane (prepared from 1.32 g of 5-methylimidazo-[1,5-a]pyridine and 5.05 ml of 2.4 N n-butyllithium in hexane) is added all at once. The mixture is stirred at room temperature overnight.

The reaction mixture is diluted with water, sodium carbonate is added and the basic solution is then extracted 3 times with chloroform. The aqueous phase is washed 3 times with ether after acidification to pH 2. Finally the aqueous phase is adjusted to pH 5 and extracted with ethyl acetate/ether. The extracts are dried and evaporated to give a yellow oil. Material is crystallized from ethanol/ether to give 5-(5-carboxy-4,4-dimethylpentyl)-imidazo[1,5-a]pyridine, melting at 124°–9°.

EXAMPLE 17

Iodine crystals (1.9 g) are added to a well-stirred solution of 1.16 g of 5-(5-carboxypentyl)-imidazo[1,5-a]pyridine and 1.68 g of sodium bicarbonate in 10 ml of water and 1 ml of ethanol. Additional 4 ml of ethanol are added to dissolve the bulk of the iodine and stirring is continued for 45 minutes. The reaction mixture is diluted with 125 ml of water and extracted twice with methylene chloride at pH 8 (NaHCO$_3$ added if necessary). The aqueous phase is concentrated in vacuo, charcoaled and adjusted to pH 4.5 with 2 N HCl. The precipitate is collected, dried and recrystallized from methanol/ether to give 1-iodo-5-(5-carboxypentyl)-imidazo[1,5-a]pyridine melting at 163°–165°.

EXAMPLE 18

Preparation of 10,000 tablets each containing 10 mg of the active ingredient of Example 2:

Formula

| | |
|---|---|
| 5-(5-carboxypentyl)imidazo[1,5-a]pyridine | 100.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

EXAMPLE 19

Preparation of 10,000 capsules each containing 25 mg of the active ingredient of Example 3b:

Formula

| | |
|---|---|
| 5-(6-carboxyhexyl)-imidazo[1,5-a]pyridine | 250.0 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 215 mg, using a capsule filling machine.

EXAMPLE 20

A solution of 5-methylimidazo[1,5-a]pyridine (4.0 g) and tetramethylethylene diamine (4.9 g) in 100 ml of tetrahydrofuran is cooled to 0° under nitrogen and 26.5 ml of 1.6 N n-butyllithium in hexane is added dropwise maintaining the temperature below 2°. After 30 minutes this solution is transferred under nitrogen over 45 minutes to an ice-cold solution of 5-bromovaleronitrile (4.86 g) in 80 ml of tetrahydrofuran. After 15 minutes the solvent is evaporated and the residue is partitioned between water and ethyl acetate. The organic phase is reextracted with 2 N hydrochloric acid (3×15 ml). Basification of the aqueous phase to pH=10 with 50% sodium hydroxide, extraction with ethyl acetate (2×75 ml), drying over magnesium sulfate, evaporation and chromatography (SiO$_2$, ethyl acetate) yields 5-(5-cyanopentyl)-imidazo[1,5-a]pyridine.

EXAMPLE 21

To a solution of 4 g of 5-(4-ethoxycarbonylbutyl)-3-ethylthio-imidazo[1,5-a]pyridine in 100 ml of ethanol is added approximately 5 g of Raney nickel. The solution is heated under reflux for 18 hours. The Raney nickel is removed by filtration and the filter cake washed with 100 ml of ethyl acetate. The filtrate is evaporated to dryness under reduced pressure to yield the product as a heavy oil. This material is purified by column chromatography on silica gel using an etherhexane mixture (1:3) as eluent. Evaporation of the solvent under reduced pressure yields 5-(4-ethoxycarbonylbutyl-)imidazo[1,5-a]pyridine as a yellow oil; NMR (CDCl$_3$) 1.25 (t, 3H), 4.15 (q, 2H), 8.1 (s, 1H).

The starting material is prepared as follows:

A solution of 17.8 g of 3-ethylthio-imidazo[1,5-a]pyridine in 200 ml of tetrahydrofuran (dried) is cooled to −70°, and 80 ml of 1.6 M n-butyl lithium in hexane is added dropwise to the stirred solution over a period of 15 minutes. On completion of the addition, the reaction is allowed to stir at −70° for a further 30 minutes. To the reaction mixture is added dropwise a solution of 20 g of ethyl 4-bromopentanoate in 75 ml of tetrahydrofuran. The reaction mixture is allowed to warm up to −10° where it is maintained for 30 minutes and subsequently is allowed to stand for 1 hour at room temperature. To the reaction mixture is added 400 ml of diethyl ether and 400 ml of 4 N hydrochloric acid. The aqueous layer is separated and the ethereal layer is washed with water. The combined aqueous extracts are rendered basic with ammonium hydroxide and extracted with 3×200 ml of ether. The ethereal extract is dried over anhydrous magnesium sulfate and the solvent evaporated under reduced pressure to yield the crude product as a heavy oil. This material is purified by column chromatography on silica gel using a 4:1 mixture of pentanediethyl ether as eluent. On evaporation of the solvent the product was distilled to give 3-ethylthio-5-(5-ethoxycarbonylbutyl)imidazo[1,5-a]pyridine, boiling at 170°/0.3 mm Hg; NMR (CDCl$_3$) 1.25(t,3H), 1.30 (t,3H), 3.15 (q,2H), 4.15 (q,2H).

EXAMPLE 22

A solution of 3 g of 5-[5-ethoxycarbonyl-5-(phenylsulfinyl)pentyl]-imidazo[1,5-a]pyridine in 50 ml xylene is heated at reflux temperature for 30 minutes under an atmosphere of nitrogen. The xylene is then removed by distillation under reduced pressure, the residue is dissolved in 15 ml of diethyl ether and purified by column chromatography on silica gel. The product is eluted using a 2:1 mixture of diethyl ether and ethyl acetate as eluent. Evaporation of the solvent yields 5-(5-ethoxycarbonylpent-4-enyl)-imidazo[1,5-a]pyridine as an oil; NMR (CDCl$_3$) 1.29 (t,3H), 4.25 (q,2H), 5.88 (d, 1H).

The starting material is prepared as follows:

To an ice-cooled, magnetically stirred slurry of 0.96 g of sodium hydride in 50 ml dimethylformamide is added 3.92 g of ethyl 2-(phenylthio)acetate in a dropwise manner over a period of 15 minutes. The suspension is stirred at room temperature for 2 hours and then cooled to 5° by means of an ice-bath. To this suspension is added 4.16 g of 5-(4-chlorobutyl)-imidazo[1,5-a]pyridine in a dropwise manner over a period of 1 hour. On completion of the addition, 3.2 g of sodium iodide is added to the reaction mixture which is then allowed to stir overnight at room temperature.

The reaction mixture is poured into 150 ml of ice water and extracted with 3×100 ml aliquots of a 1:1 mixture of diethyl ether and ethyl acetate. The organic phase is washed with 2×100 ml of brine and then extracted with 3×50 ml portions of 1 N hydrochloric acid. The acidic aqueous extracts are combined, basified with ammonium hydroxide and extracted with 3×150 ml portions of a 1:1 mixture of diethyl ether and ethyl aetate. These organic extracts are dried over anhydrous magnesium sulfate, filtered and the solvent concentrated under reduced pressure to yield the product as an oil, which is purified by column chromatography on silica gel using diethyl ether as eluent. Evaporation of the solvent yields 5-[5-ethoxycarbonyl-5-(phenylthio)pentyl]-imidazo[1,5-a]pyridine as a heavy oil; NMR (CDCl$_3$) 3.3–3.8 (1H); IR 1720 cm$^{-1}$.

To a solution of 3.8 g of 5-[5-ethoxycarbonyl-5-(phenylthio)pentyl]-imidazo[1,5-a]pyridine in 100 ml of methanol is added 2.8 g of sodium metaperiodate. The reaction mixture is allowed to stir at room temperature for 18 hours. The solvent is evaporated under reduced pressure and 150 ml of water is added to the residue, which is extracted with 3×100 ml of ethyl acetate. The organic phase is extracted with 2×50 ml portions of 1 N hydrochloric acid followed by basification of the aqueous extract with ammonium hydroxide and re-extraction into 2×100 ml portions of ethyl acetate. These combined ethyl acetate extracts are dried over anhydrous magnesium sulfate, filtered and the solvent concentrated under reduced pressure to yield an oil which is purified by column chromatography on silica gel using ethyl acetate, diethyl ether (1:1) as eluent. Evaporation of the solvent yields 5-[5-ethoxycarbonyl-5-(phenylfulfinyl)pentyl]-imidazo[1,5-a]pyridine as an oil; IR 1720 cm$^{-1}$, 1040 cm$^{-1}$.

EXAMPLE 23

To a solution of 300 mg of 5-(5-ethoxycarbonylpent-4-enyl)-imidazo[1,5-a]pyridine in 20 ml methanol is added 5 ml of 1 N sodium hydroxide. The reaction mixture is stirred at room temperature for 18 hours. The methanol is evaporated under reduced pressure and an additional 5 ml of water is added to the aqueous residue, which is then extracted with 3×5 ml aliquots of ethyl acetate. The basic aqueous layer is then adjusted to pH 5 and extracted with 3×5 ml portions of ethyl acetate. These extracts are dried over anhydrous magnesium sulfate, filtered and the solvent evaporated under reduced pressure to yield 5-(5-carboxypent-4-enyl)-imidazo[1,5-a]pyridine melting at 142°–144°.

EXAMPLE 24

To a solution of 2.75 g of 5-(5-formylpentyl)-imidazo[1,5-a]pyridine in 180 ml of chloroform is added 6.5 g of carbethoxymethylene-triphenylphosphorane. The reaction mixture is stirred at room temperature for 18 hours. The solvent is then evaporated under reduced pressure to yield 5-(7-ethoxycarbonyl-hept-6-enyl-imidazo[1,5-a]pyridine as an oil.

The starting material is prepared as follows:

To a cooled (−60°) solution of 4.9 g of 5-(5-methoxycarbonylpentyl)-imidazo[1,5-a]pyridine (obtained by esterification of 5-(5-carboxypentyl)-imidazo[1,5-a]pyridine of Example 2 with diazomethane in methylene chloride) in 140 ml of methylene chloride is added 40 ml of a 1.75 M solution of di-isobutyl aluminum hydride in hexane in a dropwise manner over a 20 minute period. On completion of the addition, the reaction is allowed to stir at −60° for a further 20 minutes. Then, 10 ml of methanol, followed by 100 ml of water, are added to quench the reaction. The reaction mixture is stirred at room temperature for 15 minutes, the methylene chloride layer is separated and the solvent evaporated under reduced pressure to yield 5-(5-formylpentyl)-imidazo[1,5-a]pyridine as an oil; NMR (CDCl$_3$) 9.7 (m, 1H); IR (CH$_2$Cl$_2$) 1710 cm$^{-1}$.

EXAMPLE 25

To a solution of 2.8 g of 5-(7-ethoxycarbonyl- hept-6-enyl)imidazo[1,5-a]pyridine in 30 ml of methanol is added 15 ml of 1 N sodium hydroxide. The reaction is stirred at room temperature for 3 hours. The methanol is evaporated under reduced pressure and the residue diluted with 30 ml of water and the solution adjusted to pH 7 with 1 N hydrochloric acid. The solution is extracted with 2×50 ml of ethyl acetate. The combined ethyl acetate extracts are dried over anhydrous magnesium sulfate, filtered and the solvent evaporated under reduced pressure to yield 5-(7-carboxyhept-6-enyl)-imidazo-[1,5-a]pyridine melting at 110°–111°.

EXAMPLE 26

To a solution of 150 mg of 5-(5-carboxypent-4-enyl)-imidazo[1,5-a]pyridine in 7 ml methanol is added 100 mg of 10% palladium on carbon as catalyst. The reaction mixture is hydrogenated at atmospheric pressure for 3 hours. The catalyst is removed by filtration and the solvent evaporated under reduced pressure to yield 5-(5-carboxypentyl)-imidazo[1,5-a]pyridine melting at 144°–7°, and identical to the product of Example 2.

EXAMPLE 27

To a solution of 180 mg of 5-(7-carboxyhept-6-enyl)-imidazo[1,5-a]pyridine in 30 ml of methanol is added 200 mg of 10% palladium on carbon as catalyst. The reaction mixture is subjected to hydrogenation at atmospheric pressure for 3 hours. The catalyst is removed by filtration and the solvent evaporated under reduced pressure to yield product melting at 69°–71° consisting of a mixture of 5-(7-carboxyheptyl)imidazo-[1,5-a]pyridine (the compound of Example 3c) and 5-(7-carboxyheptyl)-5,6,7,8-tetrahydroimidazo[1,5-a]pyridine.

EXAMPLE 28

A solution of 0.1 g of 2-aminomethyl-3-(4-methoxycarbonylbutyl)pyridine in 0.6 ml of formic acid is heated at 90° for 18 hours. The mixture is cooled to 0°, made basic with saturated ammonium hydroxide solution and extracted with methylene chloride (4×10 ml). Drying, filtration and evaporation of the extracts yields 2-(N-formylaminomethyl)-3-(4-methoxycarbonylbutyl)pyridine, melting at 43°–45° C. which is redissolved in 1 ml of toluene and heated at 90° for 17 hours with 75 mg of phosphorus oxychloride. Evaporation of excess phosphorus oxychloride with toluene, basification at 0° with saturated ammonium hydroxide solution, extraction with methylene chloride (4×15 ml) and drying over sodium sulfate yields an oil, which is chromatographed (silica gel, ethyl acetate) to yield as an oil, 8-(4-methoxycarbonylbutyl)-imidazo[1,5-a]pyridine; Rf 0.29; NMR (CDCl$_3$) 3.70 (s, 3 H), 6.50 (d, 2 H), 7.43 (s, 1 H), 7.83 (t, 1 H), 8.22 (s, 1 H); IR (CH$_2$Cl$_2$) 1725 cm$^{-1}$.

The starting material is prepared as follows:

A solution of 3-bromopyridine (7.9 g), methyl 4-pentenoate (7.15 g), palladium acetate (0.11 g) and tri-o-tolylphosphine (0.6 g) in 50 ml of triethylamine is refluxed for 24 hours under argon and the solvent evaporated. The residue is taken up in methylene chloride (50 ml) and washed with water (2×40 ml). The organic phase is dried and evaporated to yield 3-(4-methoxycarbonylbut-1-enyl)pyridine as a colorless liquid; NMR (CDCl$_3$) 3.72 (s, 3 H), 6.40 (s, 1 H); IR (film) 1725 cm$^{-1}$.

3-(4-Methoxycarbonylbut-1-enyl)pyridine (9.5 g) is hydrogenated in 100 ml of methanol at 3 atmospheres for 3.5 hours with 0.5 g of 5% palladium on charcoal to yield, after filtration and evaporation, 3-(4-methoxycarbonylbutyl)pyridine as an oil; NMR (CDCl$_3$) 3.80 (s, 3 H); IR (CH$_2$Cl$_2$) 1730 cm$^{-1}$.

Peracetic acid (40%, 8.3 ml) is added dropwise to 3-(4-methoxycarbonylbutyl)pyridine (10.81 g) so as to maintain the reaction temperature between 80° and 85°. After the addition is complete, the temperature is allowed to fall to 30° and excess peracid is destroyed with aqueous sodium sulfite. The acetic acid is distilled at reduced pressure, and the residue is taken up in methylene chloride (50 ml), filtered and evaporated. The residue consisting of 3-(4-methoxycarbonylbutyl)pyridine-N-oxide is treated with dimethyl sulfate (7.7 g) in 40 ml of toluene at 90° for 1 hour and the solvent is evaporated. The 3-(4-methoxycarbonylbutyl)-1-methoxypyridinium methyl sulfate salt is dissolved in 16.7 ml of ice-cold water and 8.3 ml of 1 N sodium hydroxide, and a solution of potassium cyanide (11.21 g) in 16.7 ml of ice-cold water is added slowly so as to keep the reaction temperature below 0°. After 24 hours at 0°, extraction with methylene chloride (3×30 ml), drying over sodium sulfate and evaporation of solvent yields a mixture of isomeric cyanopyridines from which 2-cyano-3-(4-methoxycarbonylbutyl)pyridine having Rf=0.56 and NMR (CDCl$_3$) 8.52 (m, 1 H), and 2-cyano-5-(4-methoxycarbonylbutyl)pyridine having Rf=0.50 and NMR (CDCl$_3$) 8.72 (s, 1 H) were separated by chromatography (silica gel, ether-pentane 3:2).

2-Cyano-3-(4-methoxycarbonylbutyl)pyridine (2.40 g) is dissolved in 92 ml of methanol containing 2.4 ml of conc. hydrochloric acid and hydrogenated at atmospheric pressure with 1.2 g of 10% palladium on charcoal for 3 hours. Filtration, evaporation and recrystallization from ether-methylene chloride yields 2-aminomethyl-3-(4-methoxycarbonylbutyl)pyridine hydrochloride, m.p. 79°–81°.

EXAMPLE 29

A solution of 8-(4-methoxycarbonylbutyl)-imidazo[1,5-a]pyridine (30 mg) in 0.3 ml of ethanol and 0.3 ml of 1 N sodium hydroxide is refluxed for 2 hours, cooled, diluted with 2 ml of water and extracted with ethyl acetate (1×5 ml). The aqueous phase is brought to pH=6 and is extracted with methylene chloride (4×10 ml). The extracts are dried and evaporated to yield 8-(4-carboxybutyl)imidazo[1,5-a]pyridine, melting at 195°–197°.

EXAMPLE 30

2-Aminomethyl-5-(4-methoxycarbonylbutyl)pyridine (0.20 g) is heated at 90° in 0.6 ml of formic acid for 18 hours. The mixture is cooled to 0°, made basic with saturated ammonium hydroxide solution and extracted with methylene chloride (4×15 ml). Drying, filtration and evaporation of the extracts yields 2-(N-formylaminomethyl)-5-(4-methoxycarbonylbutyl)pyridine as an oil (IR 1720, 1675 cm$^{-1}$) which is redissolved in 1 ml of toluene and heated at 90° for 18 hours with phosphorus oxychloride (0.166 g). Evaporation of excess phosphorus oxychloride with toluene, basification at 0° with saturated ammonium hydroxide solution, extraction with methylene chloride (4×15 ml) and drying over sodium sulfate yields an oil which is chromatographed (silica gel, ethyl acetate) to yield 6-(4-methoxycarbonylbutyl)-imidazo[1,5-a]pyridine; Rf=0.26; NMR (CDCl$_3$) 3.58 (s, 3 H), 6.45 (d, 1 H), 7.25 (d, 1 H), 7.38 (s, 1 H), 7.62 (s, 1 H), 7.94 (s, 1 H); IR (CH$_2$Cl$_2$) 1730 cm$^{-1}$.

The starting material is prepared as follows:

2-Cyano-5-(4-methoxycarbonylbutyl)pyridine (1.48 g, see Example 28) is dissolved in 56 ml of methanol containing 1.5 ml of concentrated hydrochloric acid and hydrogenated at atmospheric pressure with 0.75 g of 10% palladium on charcoal for 18 hours. Filtration, evaporation, chromatography on 20 g of silica gel with 1:1 methanol-ethyl acetate, and crystallization from ether-methylene chloride yields 2-aminomethyl-5-(4-methoxycarbonylbutyl)pyridine as its carbonate melting at 79°-80°; NMR (CDCl$_3$) 3.67 (s, 3 H), 4.24 (s, 2 H); IR (CH$_2$Cl$_2$) 1725 cm$^{-1}$.

EXAMPLE 31

A solution of 6-(4-methoxycarbonylbutyl)-imidazo[1,5-a]pyridine in 0.3 ml of ethanol and 0.8 ml of 1 N sodium hydroxide, is refluxed gently for 2 hours, cooled, diluted with 2 ml of water and extracted with ethyl acetate (5 ml). The aqueous phase is brought to pH=6 and is extracted with chloroform. The extracts are dried and evaporated to yield 6-(4-carboxybutyl)-imidazo[1,5-a]pyridine, melting at 168°-171°.

EXAMPLE 32

2-(N-formylaminomethyl)-4-(3-methoxycarbonylpropyl)pyridine (33 mg) is dissolved in 1 ml of toluene and heated at 90° with phosphorus oxychloride (44 mg) for 18 hours under nitrogen. The solvent is evaporated and the residue is suspended in methylene chloride, cooled to 0° and made basic with saturated ammonium hydroxide solution. The aqueous phase is extracted with methylene chloride (4×15 ml) which is dried over sodium sulfate and evaporated to yield 7-(3-methoxycarbonylpropyl)imidazo[1,5-a]pyridine as an oil, after purification by preparative thin layer chromatography (silica gel, 3:1 ethyl acetatemethanol); NMR (CDCl$_3$) 3.70 (s, 3 1 H), 6.45 (q, 1 H), 7.2 (s, 1 H), 7.32 (s, 1 H), 7.90 (d, 1 H), 8.08 (s, 1 H); IR (CH$_2$Cl$_2$) 1730 cm$^{-1}$.

The starting material is prepared as follows:

Potassium cyanide (11.18 g) and dibenzo-18-crown-6 (1.0 g) are added to a solution of 4-(3-chloropropyl)-pyridine (6.68 g) prepared from 4-(3-hydroxypropyl)-pyridine, in 300 ml of dry acetonitrile under nitrogen. The mixture is refluxed for 24 hours, the solvent evaporated and the residue partitioned between methylene chloride and water. The aqueous phase is further extracted with methylene chloride (3×100 ml) and the combined extracts are dried over sodium sulfate, decolorized with charcoal and evaporated to yield 4-(3-cyanopropyl)pyridine as a colorless oil.

Hydrogen chloride is bubbled slowly into an ice-cooled methanolic solution of 4-(3-cyanopropyl)pyridine (5.5 g) for 2 hours and 100 ml of water is added carefully. The solution is stirred for 15 minutes and the solvent is evaporated. The residue is made basic with saturated sodium bicarbonate solution and extracted with methylene chloride (3×100 ml) which is dried over sodium sulfate. Evaporation of the solvent and filtration through 50 g of silica gel in ether yields 4-(3-methoxycarbonylpropyl)pyridine as an oil; NMR (CDCl$_3$) 3.68 (s, 3 H), 7.05-7.25 (m, 2 H), 8.45-8.65 (m, 2 H); IR, 1725 cm$^{-1}$.

Peracetic acid (40%, 2.9 ml) is added to 4-(3-methoxycarbonylpropyl)pyridine (3.20 g) at room temperature. The mixture is heated at 80° for 1 hour and the acetic acid is evaporated after a test for peroxide is negative. The residue is taken up in methylene chloride (50 ml), filtered, and the solvent evaporated. The resulting 4-(3-methoxycarbonylpropyl)pyridine-N-oxide is treated with dimethylsulfate (2.8 g, 22.2 mmol) in 12 ml of toluene at 80° C. for 1 hour. The solvent is evaporated to yield 5.45 g of the 4-(3-methoxycarbonylpropyl)-1-methoxypyridinium methyl sulfate salt which is added at 0° to a solution of 89.75 g potassium cyanide in 20 ml of water. The reaction is stirred at 0° for 1 hour and 25° for 3 hours and then extracted with methylene chloride (1×30 ml). The aqueous phase is reextracted, after standing for 24 hours, with methylene chloride (1×30 ml), and the combined extracts are dried over sodium sulfate and evaporated to yield a red oil. Chromatography on 70 g of silica gel with ether as the eluent yields 2-cyano-4-(3-methoxycarbonylpropyl)pyridine as an oil; NMR (CDCl$_3$) 3.67 (s, 3 H), 7.42 (d, 1 H), 7.60 (s, 1 H), 8.60 (d, 1 H); IR (CH$_2$Cl$_2$) 1725 cm$^{-1}$.

2-Cyano-4-(3-methoxycarbonylpropyl)pyridine (0.83 g) is hydrogenated at 3 atmospheres for 3 hours in 9 ml of methanol with 0.4 g of 10% palladium on charcoal. Filtration, evaporation, and preparative thin layer chromatography on silica gel with 1:1 methanol-ethyl acetate yields 2-aminomethyl-4-(3-methoxycarbonylpropyl)pyridine; Rf, 0.37 (EtOAc-MeOH 1:1, 1% NH$_4$OH); NMR (CDCl$_3$) 3.67 (s, 3 H), 4.15 (s, 2 H).

2-Aminomethyl-4-(3-methoxycarbonylpropyl)pyridine (0.11 g) is heated at 90° in 0.5 ml of 97% formic acid for 18 hours. The reaction is cooled to room temperature, made basic with ammonium hydroxide solution and extracted with methylene chloride (4×20 ml). The organic extracts are dried over sodium sulfate and evaporated to yield 2-(N-formylaminomethyl)-4-(3-methoxycarbonylpropyl)pyridine; IR (CH$_2$Cl$_2$) 1735, 1685 cm$^{-1}$.

EXAMPLE 33

7-(3-methoxycarbonylpropyl)-imidazo[1,5-a]pyridine (Example 32, 8.0 mg) is dissolved in 0.3 ml of methanol and 0.1 ml of 1 N NaOH is added. The mixture is stirred at 25° for 5 hours, evaporated, and the residue is redissolved in 5 ml of water. The aqueous solution is washed with 2 ml of ethyl acetate, brought to pH=6 with 2 N sulfuric acid and extracted with methylene chloride (3×5 ml). The organic extracts are dried over sodium sulfate/magnesium sulfate and evaporated to yield 7-(3-carboxypropyl)-imidazo[1,5-a]pyridine, IR (CHCl$_3$) 1720 cm$^{-1}$.

EXAMPLE 34

A solution of 7-[4,4-(bis-methoxycarbonyl)butyl]-imidazo-[1,5-a]pyridine (65 mg) in 0.8 ml of 1 N sodium hydroxide and 0.5 ml of ethanol is heated at reflux for 2 hours. The solvent is evaporated and 0.8 ml of 1 N hydrochloric acid is added. After the water is evaporated, the residue is redissolved in 3 ml of xylene and heated at 137° for 4 hours. The xylene is evaporated and replaced with 2 ml of 1 N sodium hydroxide. Extraction of the aqueous phase with ethyl acetate (5 ml), acidification to pH=6, reextraction with chloroform (3×15 ml) and evaporation yields 7-(4-carboxybutyl-)imidazo[1,5-a]pyridine, melting at 158°–161°.

The starting material is prepared as follows:

According to procedures previously described (e.g., Examples 28, 32), 4-(3-chloropropyl)pyridine is converted to 4-(3-chloropropyl)-2-cyanopyridine; NMR (CDCl$_3$) 3.56 (t, 2 H), 7.40 (d, 1 H), 7.57 (s, 1 H), 8.60 (d, 1 H).

A solution of borane-dimethylsulfide (0.83 ml, 7.7 mmol) in 7 ml of tetrahydrofuran is added slowly to a refluxing solution of 4-(3-chloropropyl)-2-cyanopyridine (1.24 g, 6.9 mmol) in 7 ml of tetrahydrofuran while dimethylsulfide simultaneously distills off. The mixture is refluxed for 15 minutes after the addition is complete, cooled to 30° and 6 ml of 6 N hydrochloric acid is added. After hydrogen evolution ceases, the mixture is refluxed for 30 minutes, cooled to 0° and saturated with solid sodium carbonate before extracting with methylene chloride (4×50 ml). The organic extracts are dried over sodium sulfate and evaporated to yield an oil which is filtered through 10 g of silica gel (1:1 EtOAc-MeOH) to yield 2-aminomethyl-4-(3-chloropropyl)-pyridine as a yellow oil; NMR (CDCl$_3$) 3.55 (t, 2 H), 4.20 (s, 2 H).

A solution of 2-aminomethyl-4-(3-chloropropyl)pyridine (0.47 g) in 1 ml of formic acid is heated at 90° for 18 hours, cooled to 0° and made basic by the addition of saturated ammonium hydroxide solution. Extraction with methylene chloride (4×10 ml), drying over sodium sulfate and evaporation yields 2-(N-formylaminomethyl)-4-(3-chloropropyl)pyridine (IR 1674 cm$^{-1}$) which is heated at 90° in phosphorus oxychloride (0.75 g) for 15 hours. Excess phosphorus oxychloride is evaporated with toluene and the residue is suspended in methylene chloride (15 ml), cooled to 0° and made basic with saturated ammonium hydroxide. Extraction with methylene chloride (4×15 ml), drying over sodium sulfate and preparative thin layer chromatography (silica gel, EtOAc) of the residue yields 7-(3-chloropropyl)-imidazo[1,5-a]pyridine (Rf=0.24, EtOAc) as a gum; NMR (CDCl$_3$) 3.58 (t, 2 H), 6.42 (q, 1 H), 7.21 (s, 1 H), 7.32 (s, 1 H), 7.88 (d, 1 H), 8.07 (s, 1 H).

A solution of 7-(3-chloropropyl)-imidazo[1,5-a]pyridine (50 mg), dimethyl malonate (0.14 g), and potassium carbonate (144 mg) in 2 ml of dimethylformamide is heated between 80° and 90° under nitrogen for 9 hours. The solvent is evaporated and the residue taken up in 10 ml of water and extracted with ethyl acetate (2×10 ml). The organic extracts are washed with 2 N hydrochloric acid (2×10 ml). Basification of the aqueous extracts with solid sodium bicarbonate, extraction with methylene chloride (3×10 ml), drying over sodium sulfate and evaporation yields 7-[4,4-(bis-methoxycarbonyl)-butyl]imidazo[1,5-a]pyridine; NMR (CDCl$_3$) 3.40 (s, 6 H), 6.06 (d, 1 H); IR (CH$_2$C$_{12}$) 1725 cm$^{-1}$.

EXAMPLE 35

A solution of 5-[5,5-(bis-ethoxycarbonyl)pentyl]-imidazo[1,5-a]pyridine (0.60 g) in 6.5 ml of 1 N sodium hydroxide and 4 ml of ethanol is refluxed for 2 hours. The solvent is evaporated and 6.5 ml of 1 N hydrochloric acid is added. The water is then evaporated and the resulting 5-[5,5-(biscarboxy)pentyl]-imidazo[1,5-a]pyridine is heated at 137° for 4 hours in 25 ml of xylene. The xylene is replaced with 16 ml of 1 N sodium hydroxide. Extraction of the aqueous phase with ethyl acetate (15 ml), acidification to pH=6, reextraction with chloroform (3×40 ml), drying over magnesium sulfate and evaporation yields 5-(5-carboxypentyl)-imidazo[1,5-a]pyridine melting at 146°–7° (compound of Example 2).

The starting material is prepared as follows:

A solution of 5-(4-chlorobutyl)-imidazo[1,5-a]pyridine (0.42 g), diethyl malonate (1.34 g) and potassium carbonate (1.15 g) in 20 ml of dimethylformamide is heated between 80° and 90° under nitrogen for 10 hours. The solvent is evaporated and the residue taken up in 50 ml of water. The aqueous phase is extracted with ethyl acetate (3×40 ml). The extracts are washed with cold 2 N hydrochloric acid (3×10 ml). Basification of the aqueous phase with solid sodium bicarbonate, extraction with methylene chloride (3×20 ml), drying over sodium sulfate and evaporation yields the 5-[5,5-(bis-ethoxycarbonyl)pentyl]imidazo[1,5-a]pyridine, melting at 59°–61°.

The starting material, 5-(4-chlorobutyl)-imidazo[1,5-a]pyridine, is prepared by the procedure described for the starting material in Example 4, using 1-bromo-3-chloropropane as the reagent instead of 1-bromo-4-chlorobutane therein.

EXAMPLE 36

Pyridinium dichromate (0.94 g) is added as a solid to a solution of 5-(6-hydroxyhexyl)-imidazo[1,5-a]pyridine (123 mg) in 10 ml of N,N-dimethylformamide at 25° under nitrogen. The solution is stirred for 6 hours, poured into 150 ml of water and extracted with methylene chloride (5×20 ml). The organic extracts are washed with 1 N sodium hydroxide. Acidification of the aqueous phase to pH=6, extraction with methylene chloride and drying over sodium sulfate/magnesium sulfate yields 5-(5-carboxypentyl)-imidazo[1,5-a]pyridine of Example 2 melting at 145°–146°.

EXAMPLE 37

5-Methylimidazo[1,5-a]pyridine [J. Org. Chem. 40, 1210 (1975), 424.7 g] is charged into a 12 liter flask equipped with mechanical stirrer, thermometer and nitrogen atmosphere. Dry tetrahydrofuran (THF, 3,000 ml) is charged into the flask and the resulting solution is cooled to −65° in a dry ice/acetone bath. n-Butyllithium (1.0 mole, 2.4 N in hexane) is poured into the flask all at once under a nitrogen atmosphere. The temperature rises to −32°. The mixture is recooled to −50° and a second mole of n-butyllithium is charged in the same manner. A second temperature rise occurs and after again cooling to −50°, a third mole of the n-butyllithium is charged into the reactor. The reaction mixture is then stirred for twenty minutes, the temperature drops to −65°. To this stirring solution a cold (−67°) solution of 5-bromo-1,1,1-triethoxypentane (606.9 g) in 500 ml of THF is added as rapidly as possible, raising the temperature to −25°. The reaction mixture is then warmed to −15° and stirred for 2 hours. Acetic acid (50 ml) is added and most of the solvent is removed under vacuum. The residue is taken up in 2,000 ml of ethyl ether; acetic acid (100 ml), and 12 N HCl (100 ml) are added while the reaction mixture is cooled to 0°. After 15 to 20 minutes, ice-cold 7.5 N ammonium hydroxide (1000 ml) is added. The organic phase is separated and the aqueous is washed again with ethyl ether (500 ml). The pH of the aqueous is adjusted to 9 with ammonium hydroxide and extracted again with ethyl ether (500 ml). The combined ether extracts are washed with a dilute sodium chloride solution basified to pH 13–14 with potassium hydroxide. The ether extract is treated with charcoal and magnesium sulfate. The mixture is filtered and evaporated to give a dark oil which is dried at 2mm Hg. The oil is distilled under high vacuum to give 5-(5-ethoxycarbonylpentyl)-imidazo[1,5-a]pyridine of Example 1, boiling at 220°/0.2 mm Hg.

The starting 5-bromo-1,1,1-triethoxypentane is prepared as follows:

5-Bromovaleronitrile (1,200 g) is charged into a 5 liter 3 neck flask under nitrogen atmosphere. The complete reaction vessel is then placed in an ice bath. Then hydrogen chloride gas (287 g) is slowly bubbled into the reaction vessel. The reaction mixture is then diluted with ethyl ether (3,200 ml) and stirred at 4° overnight. The resulting suspension is cooled to −30° in a dry ice/acetone bath. The solid is collected, washed with ethyl ether, and dried in a vacuum dessicator over KOH and P$_2$O$_5$ for 3 days to give ethyl 5-bromoimidovalerate hydrochloride which is used in the next step without further purification.

Ethyl 5-bromoimidovalerate hydrochloride (556 g) is charged into a 12 liter flask equipped with a mechanical stirrer under a nitrogen atmosphere. Anhydrous ethanol (836 g) is added and the reaction is stirred at room temperature for 2 hours, at which time a clear solution is obtained. Ethyl ether (3700 ml) is charged into the flask and stirring is continued for 3 days at room temperature. The solution is cooled to −30° and filtered to remove ammonium chloride. The filtrate is evaporated to dryness in a rotary evaporator under vacuum. The residue is distilled under high vacuum (0.2 mm Hg), using a 12 cm fractionation column. The main fraction distilling at ca. 71°–82° is collected, and redistilled with a 46 cm column to yield 5-bromo-1,1,1-triethoxypentane, b.p. 60°-2°/0.2 mm.

5-(5-Ethoxycarbonylpentyl)-imidazo[1,5-a]pyridine can also be prepared from 2-(N-formylaminomethyl)-6-(5-ethoxycarbonylpentyl)pyridine essentially according to the cyclization procedure described in Examples 28, 30 and 32.

EXAMPLE 38

5-(5-Ethoxycarbonylpentyl)-imidazo[1,5-a]pyridine (1091 g) is charged into a 12 liter round bottom flask under a nitrogen atmosphere. Ethyl alcohol (95%, 420 ml) is added while stirring. With continued stirring, 2 N NaOH (2100 ml) is added in portions. After complete addition the mixture is warmed at 70° for 20 minutes, at which time a solution is obtained, and heating is continued for 2 hours. Additional sodium hydroxide (50% solution, 21 ml) is added and heating is continued for 40 more minutes. The reaction mixture is cooled, 12 N HCl (30 ml) is added, and the ethyl alcohol is partially removed by evaporation under reduced pressure. The resulting solution is washed with ethyl ether (1700 ml), decolorized with charcoal, filtered, and acidified with acetic acid (300 ml). The product that crystallizes at 4° overnight is collected, washed first with water, then with ethyl ether (1000 ml), and dried to give 5-(5-carboxypentyl)-imidazo[1,5-a]pyridine, melting at 146°–8°, and identical to the product of Example 2.

EXAMPLE 39

The following compounds can be prepared essentially according to procedures described in the previous examples.

(a) 5-(4-ethoxycarbonyl-but-3-enyl)-imidazo[1,5-a]pyridine by condensation of 5-methylimidazo[1,5-a]pyridine with ethyl 4-bromocrotonate;

(b) 5-(9-hydroxynon-7-ynyl)-imidazo[1,5-a]pyridine by condensation of 1-tetrahydropyranyloxy-8-bromooct-6-yne with 5-methylimidazo[1,5-a]pyridine and subsequent hydrolysis.

What is claimed is:

1. A compound of the formula

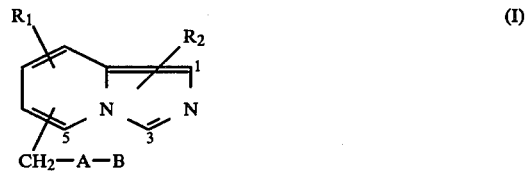

or a 5,6,7,8-tetrahydro derivative thereof, wherein $R_1$ and $R_2$ are hydrogen, halogen or lower alkyl; A is straight chain or branched alkylene of 1 to 12 carbon atoms, alkynylene, or alkenylene of 2 to 12 carbon atoms; B represents carboxy, lower alkoxycarbonyl, unsubstituted or mono- or di-(lower alkyl)carbamoyl, cyano or hydroxymethyl; or a pharmaceutically acceptable salt thereof.

2. A compound of claim 1 wherein the group CH₂—A—B is at the 5-position.

3. A compound of claim 1 wherein A is straight or branched alkylene of 1 to 12 carbon atoms.

4. A compound of claim 1 of the formula

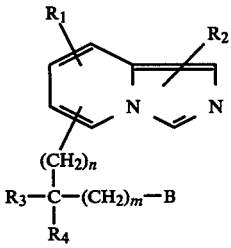

(II)

or a 5,6,7,8-tetrahydro derivative thereof, wherein $R_1$, $R_2$, $R_3$ and $R_4$ are hydrogen or lower alkyl of 1 to 4 carbon atoms; n is 1 to 7; m is 0 or 1; B represents carboxy, lower alkoxycarbonyl, unsubstituted or mono- or di-(lower alkyl)carbamoyl, cyano or hydroxymethyl; or a pharmaceutically acceptable salt thereof.

5. A compound of claim 4 wherein the group

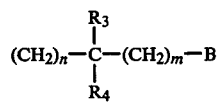

is attached at the 5-position.

6. A compound of claim 4, or a 5,6,7,8-tetrahydro derivative thereof, wherein $R_1$, $R_2$, $R_3$, $R_4$ are hydrogen, methyl or ethyl; $(CH_2)_n$ is propylene, butylene, pentylene or hexylene; m is 0 or 1; B represents carboxy, methoxycarbonyl, ethoxycarbonyl, unsubstituted carbamoyl, monomethyl or monoethylcarbamoyl, dimethyl or diethylcarbamoyl, cyano or hydroxymethyl; or a pharmaceutically acceptable salt thereof.

7. A compound of claim 1 of the formula

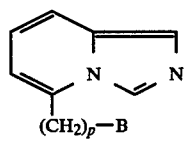

(III)

or a 5,6,7,8-tetrahydro derivative thereof, wherein p is 3 to 8; B represents carboxy, lower alkoxycarbonyl, unsubstituted or mono- or di-(lower alkyl) carbamoyl, cyano or hydroxymethyl; or a pharmaceutically acceptable salt thereof.

8. A compound of claim 7 of the formula

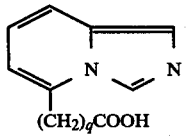

(IV)

or a 5,6,7,8-tetrahydro derivative thereof, wherein q is 4, 5 or 6; or a pharmaceutically acceptable acid or base addition salt thereof.

9. A compound of claim 8, the compound being 5-(6-carboxyhexyl)-imidazo[1,5-a]pyridine or a pharmaceutically acceptable acid or base addition salt thereof.

10. A compound of claim 8, the compound being 5-(5-carboxypentyl)-imidazo[1,5-a]pyridine or a pharmaceutically acceptable acid of base addition salt thereof.

11. A compound of claim 8, the compound being 5-(4-carboxybutyl)-5,6,7,8-tetrahydroimidazo[1,5-a]pyridine or a pharmaceutically acceptable acid or base addition salt thereof.

12. A pharmaceutical composition suitable for oral or parenteral administration to mammals for the treatment of diseases responsive to inhibition of thromboxane synthetase comprising an effective amount of a compound of claim 1 in combination with one or more pharmaceutically acceptable carriers.

13. A composition of claim 12 wherein the compound is 5-(5-carboxypentyl)-imidazo[1,5-a]pyridine or a pharmaceutically acceptable acid addition, metal or ammonium salt thereof.

14. A method of selectively inhibiting the release of thromboxane in mammals comprising the administration to said mammal of an effective amount of a compound of claim 1.

15. A method of treating diseases responsive to thromboxane synthetase inhibition in mammals comprising the administration to a mammal in need thereof of a therapeutically effective amount of a compound of claim 1.

16. A method according to claim 14 or 15 comprising the administration of a therapeutically effective amount of a compound of claim 8.

* * * * *